US010407698B2

(12) United States Patent
de Oliveira Lino et al.

(10) Patent No.: US 10,407,698 B2
(45) Date of Patent: Sep. 10, 2019

(54) FERMENTATION PROCESSES WITH REDUCED FOAMING

(71) Applicant: NOVOZYMES A/S, Bagsvaerd (DK)

(72) Inventors: Felipe Senne de Oliveira Lino, Curitiba (BR); Thiago O. Basso, Curitiba (BR); Soren Nymand-Grarup, Copenhagen Oe (DK); Camila do Nascimento, Curitba (BR)

(73) Assignee: NOVOZYMES A/S, Bagsvaerd (DK)

( * ) Notice: Subject to any disclaimer, the term of this patent is extended or adjusted under 35 U.S.C. 154(b) by 804 days.

(21) Appl. No.: 14/900,085

(22) PCT Filed: Jun. 19, 2014

(86) PCT No.: PCT/US2014/043152
§ 371 (c)(1),
(2) Date: Dec. 18, 2015

(87) PCT Pub. No.: WO2014/205198
PCT Pub. Date: Dec. 24, 2014

(65) Prior Publication Data
US 2016/0145647 A1 May 26, 2016

Related U.S. Application Data

(60) Provisional application No. 61/918,419, filed on Dec. 19, 2013, provisional application No. 61/837,457, filed on Jun. 20, 2013.

(51) Int. Cl.
*C12P 7/06* (2006.01)
*C12N 9/52* (2006.01)
*C12N 1/34* (2006.01)

(52) U.S. Cl.
CPC .................. *C12P 7/06* (2013.01); *C12N 1/34* (2013.01); *C12N 9/52* (2013.01); *Y02E 50/17* (2013.01)

(58) Field of Classification Search
None
See application file for complete search history.

(56) References Cited

U.S. PATENT DOCUMENTS

| 3,959,175 A | 5/1976 | Smith |
| 4,242,454 A * | 12/1980 | Muller ...................... C12P 7/06 435/162 |
| 4,769,324 A | 9/1988 | Mackintosh |
| 5,288,789 A | 2/1994 | McCarthy |
| 6,083,998 A | 7/2000 | Romualdo |
| 6,385,726 B1 | 5/2002 | Hasebe et al. |
| 2010/0227367 A1 | 9/2010 | Bordin |
| 2011/0097765 A1 * | 4/2011 | Duan ........................ C12P 7/06 435/106 |
| 2011/0097779 A1 | 4/2011 | Soong et al. |
| 2011/0207192 A1 * | 8/2011 | Pigeau ..................... C12P 7/06 435/161 |

FOREIGN PATENT DOCUMENTS

| WO | 96/13600 A1 | 5/1996 | |
| WO | WO-2012088303 A2 * | 6/2012 | ..... C12Y 302/01001 |

OTHER PUBLICATIONS

Yu et al., 2005, China Medical Science and Technology Publishing House, 142-143.
Basso et al, 2008, FEMS Yeast Res 8(7), 1155-1163.
Luo, 2002, Introduction to food biotechnology, 282, translation.
Li, 2012, Principles of modern environmental engineering, 291, translation.
Li, 1998, Biochemistry experiment, 128, translation.
Anonymous, 1985, Fermentation translations, 29, translation.

* cited by examiner

*Primary Examiner* — Thomas J. Visone
(74) *Attorney, Agent, or Firm* — Eric J. Fechter

(57) ABSTRACT

The present invention relates to processes of producing a fermentation product from readily fermentable sugar-material in a fermentation vat comprising a fermentation medium, comprising: feeding the readily fermentable sugar-material into the fermentation vat comprising a slurry of fermenting organism; fermenting the readily fermentable sugar material into a desired fermentation product, wherein protease is added during or after feeding of the readily fermentable sugar-material into fermentation vat or during fermentation of the readily fermentable sugar-material into the desired fermentation product. The invention also related to the use of protease for reducing foaming in the fermentation yells generating by the fermenting organism during fermentation of the readily fermentable sugar-material.

16 Claims, 5 Drawing Sheets

Specification includes a Sequence Listing.

US 10,407,698 B2

FERMENTATION PROCESSES WITH REDUCED FOAMING

CROSS-REFERENCE TO RELATED APPLICATIONS

This application is a 35 U.S.C. 371 national application of PCT/US2014/043152 filed Jun. 19, 2014, which claims priority or the benefit under 35 U.S.C. 119 of U.S. provisional application Nos. 61/837,457 and 61/918,419 filed Jun. 20, 2013 and Dec. 19, 2013, respectively, the contents of which are fully incorporated herein by reference.

FIELD OF THE INVENTION

The present invention relates to reducing foaming in fermentation processes for producing fermentation products, such as ethanol, from readily fermentable sugar materials.

REFERENCE TO A SEQUENCE LISTING

This application contains a Sequence Listing in computer readable form. The computer readable form is incorporated herein by reference.

BACKGROUND OF THE INVENTION

Fermentation products, such as ethanol, can be produced from a wide range of renewable feedstocks. These can be classified in three main groups: (1) readily fermentable sugar materials, such as sugar cane (i.e., sugar cane juice and molasses), sugar beets, sweet sorghum; (2) starchy materials, such as corn, potatoes, rice, wheat, agave; and (3) cellulosic materials, such as stover, grasses, corn cobs, wood and sugar cane bagasse. The readily fermentable sugar material contains simple sugars, such as sucrose, glucose and fructose, that can readily be fermented by yeast. In contrast to starchy and cellulosic feedstocks there is no need for prior hydrolysis of polysaccharides such as starch and/or cellulose/hemicellulose.

Readily fermentable sugar materials, such as sugar cane juice and molasses, are used as substrates in, e.g., Brazilian ethanol production. Yeast, such as especially *Saccharomyces cerevisiae*, is used as the fermentation organism. Often a yeast recycling system is used where up to 90-95% of the yeast is reused from one fermentation cycle to the next. This results in very high cell densities inside the fermentation vat (e.g., 8-17% w/v, wet basis) and in a very short fermentation time. Ethanol concentrations of 8-11% (v/v) are achieved within a period of 6-11 hours at around 32° C. After every batch fermentation, yeast cells are collected by centrifugation, acid washed (e.g., sulfuric acid at pH 1.5-3.0 for 1-2 hours) and sent back to the fermentation vat. Today a chemical defoamer (dispersant) is added during acid wash at a fixed dosage after each cycle and another chemical defoamer (antifoam) is added directly into the fermentation vat automatically (when foam reaches a level sensor) or manually until foam is fully controlled.

U.S. Pat. No. 3,959,175 discloses an aqueous defoamer composition containing liquid polybutene. The defoamer composition can further comprise in part hydrophobic silica and silicone oils.

U.S. Pat. No. 5,288,789 discloses the use of a condensate of alkylphenol and aldehyde that has been polyoxyalkylated to reduce foam in a fermentation broth.

U.S. Pat. No. 6,083,998 concerns defoamer compositions for alcoholic fermentations which as aqueous based and comprise polydimethylsiloxane oils, ethylene oxide/propylene oxide block copolymers and a silicone/silica blend.

When producing ethanol from readily fermentable sugar materials, such as sugar cane juice and molasses, foam generated by the fermenting organism is a serious problem.

Even though chemical defoamers can be used there is still a desire and need for providing processes for producing fermentation products, such as ethanol, where the foam generation is reduced/controlled.

SUMMARY OF THE INVENTION

When producing fermentation products, such as especially ethanol, from readily fermentable sugar-materials, such as sugar cane juice and molasses, foam generated by the fermenting organism is a serious problem. Thus, the object of the present invention is to reduce foam generated by fermenting organisms during fermentation when producing fermentation products, such as especially ethanol, from readily fermentable sugar materials, such as sugar cane molasses. The inventors surprisingly found that proteases can be used to effectively solve the foaming problem.

The invention related to processes of producing a fermentation product from readily fermentable sugar-material in a fermentation vat comprising a fermentation medium using a fermenting organism, comprising i) feeding the readily fermentable sugar-material into the fermentation vat comprising a slurry of fermenting organism;

ii) fermenting the readily fermentable sugar-material into a desired fermentation product, wherein a protease is added a) before, during and/or after feeding in step i), and/or b) during fermentation in step ii).

In an embodiment the readily fermentable sugar material is feed into the fermentation vat as a feeding stream. The protease may be mixed with the feeding stream of the readily fermentable sugar-material. In a preferred embodiment the protease is mixed with the feeding stream before feeding step i).

After fermentation in step ii) the (used) fermenting organisms are collected/isolated, e.g., by centrifugation. The collected fermenting organism are then acid washed, e.g., with sulfuric acid, at pH 1.5-3.0, such as 2.0-2.5 for 1-2 hours. Thereafter, the fermenting organisms are returned to the fermentation vat, and (re-)used for fermentation in one or more subsequent fermentation cycles. Thus, in an embodiment the slurry of fermentation organisms, such as yeast slurry, may be prepared by resuspending acid treated yeast biomass in water. In an embodiment of the invention the protease may be added to, or mixed with, the readily fermentable sugar-material, such as sugar cane molasses, before feeding it into the slurry of fermenting organisms in step i). In another embodiment the protease may be added to the slurry of fermenting organisms during feeding of the readily fermentable sugar-material into the slurry of fermentation organisms in step i). In another embodiment the protease may be added during fermentation in step ii). In a preferred embodiment the fermentation is carried out as a batch or fed batch process. However, the fermentation may also be carried out as a semi-continuous or continuous process.

In a preferred embodiment the protease is a bacterial protease, such as a bacterial serine protease, such as a bacterial serine protease derived from a strain of *Pyrococcus*, such as a strain of *Pyrocuccus furiosus*, especially the one shown in SEQ ID NO: 2 herein, or a protease having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 2 herein.

In another preferred embodiment the protease is a serine protease, such as a peptidase family S53 protease. Serine proteases of the peptidase family S53 comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233. In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and shown as SEQ ID NO: 7 herein. In an embodiment the protease is the mature protease 3 sequence from *Meripilus giganteus* shown as SEQ ID NO: 6 herein and SEQ ID NO: 5 in WO 2014/037438. In an embodiment the protease, such as serine protease, is capable of cutting cell wall protein on the surface of the fermenting organism, such as yeast, in particular *Saccharomyces cerevisae* yeast, fermenting the readily fermentable sugar-material into a desired fermentation product, in particular ethanol, in step ii). In an embodiment the protease, such as serine protease, is capable of cutting cell wall protein, such as mannoprotein, on the surface of the fermenting organism. In an embodiment the protease, such as serine protein, is capable of degrading protein, such as mannoprotein, released from the fermenting organism. In an embodiment the protease, such as serine protease, is capable of hydrolysing protein in fermented readily fermentable sugar material such as fermented molasses (wine). The invention also relates to the use of a protease for reducing foam generated by fermenting organisms when producing a desired fermentation product from readily fermentable sugars, e.g., as defined in the claims. In a preferred embodiment the protease is a serine protease, in particular *Pyrococcus furiosus* protease or a family S53 protease, especially *Meripilus giganteus* protease 3.

| Lane | Description |
| --- | --- |
| 1 | CAT-1, control wine |
| 2 | CAT-1, PfuS treated wine |
| 3 | CAT-1, Mg Prot 3 treated wine |
| 4 | CAT-1, Protease Z5S17 treated wine |
| 5 | CAT-1, Protease Z6Z6A treated wine |
| 6 | BRT, control wine |
| 7 | BRT, PfuS treated wine |
| 8 | BRT, Mg Prot 3 treated wine |
| 9 | BRT, Protease Z5S17 treated wine |
| 10 | BRT, Protease Z6Z6A treated wine |

DETAILED DESCRIPTION OF THE INVENTION

The object of the present invention is to reduce foaming generated by fermenting organisms, especially foaming yeast, such as of the genus *Saccharomyces*, in particular *Saccharomyces cerevisae* yeast, during fermentation when producing a desired fermentation product, such as especially ethanol, from readily fermentable sugar material, such as especially sugar cane molasses. In a preferred embodiment the invention relates to a Brazillian-type ethanol fermentation process, e.g., as describe by Basso et al in (2011) in "Ethanol Production in Brazil: The Industrial Process and Its Impact on Yeast Fermentation, Biofuel Production-Recent Developments and Prospects, Dr. Marco Aurelio Dos Santos Bernardes (Ed.), ISBN: 978-953-307-478-8, InTech." Generally Brazilian ethanol processes include recycling of the fermenting organisms, especially foaming fermenting yeast, such as *Saccharomyces cerevisae* yeast, and are carried out as batch or fed bacth processes. However, some plants do semi-continuous and continuous fermentation processes.

The inventors have found a number of surprising advantages of adding protease in accordance with the invention.

The amount of foam generated during fermentation by some foaming yeast (i.e., foaming *Saccharomyces cerevisiae* yeast) when producing ethanol from sugar cane molasses was reduced by adding serine protease from *Pyrococcus furiosus*. (Protease PfuS). This is described in Examples 1 and 2.

Figure 3:
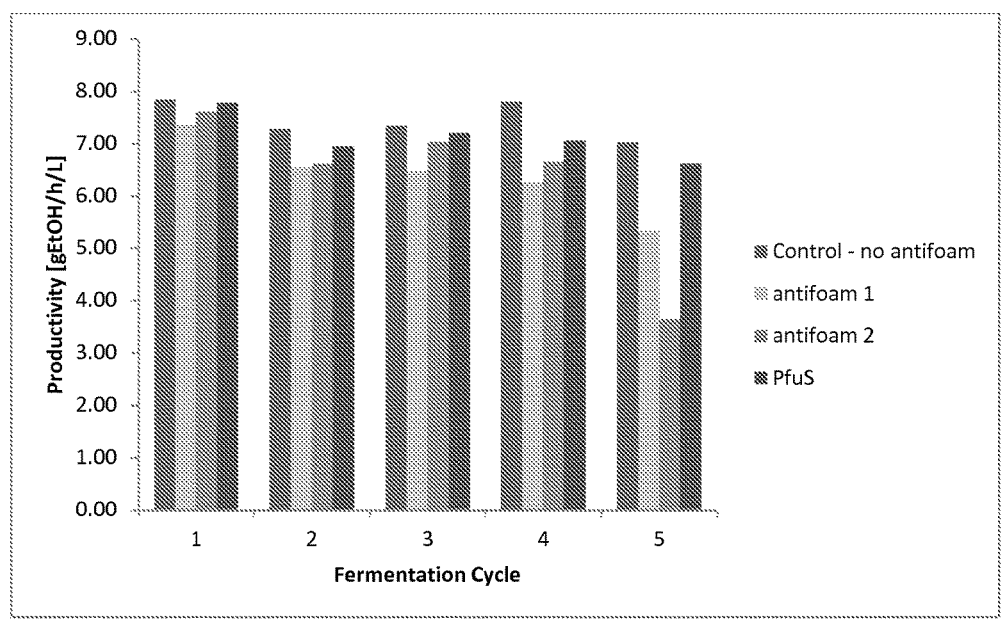
FIG. 3 shows a comparison between the average ethanol productivity [g EtOH] of a Control (neither antifoam nor enzyme added), two industrial antifoam agents (antifoam 1 and antifoam 2), and protease (PfuS) over 5 cycles of fermentation.

The inventors also found that the ethanol yield was increased when using a protease in accordance with the present invention as defoamer compared to using a commercial chemical defoamer. Example 3 and FIG. 3 compare the average ethanol productivity of a Control (neither antifoam nor enzyme added), two industrial antifoam agents (antifoam 1 and antifoam 2), and Protease PfuS over 5 cycles of fermentation. The ethanol productivity was higher for recycled *Saccharomyces cerevisae* yeast in a process of the invention when compared with two commercial antifoam products.

Figure 4:
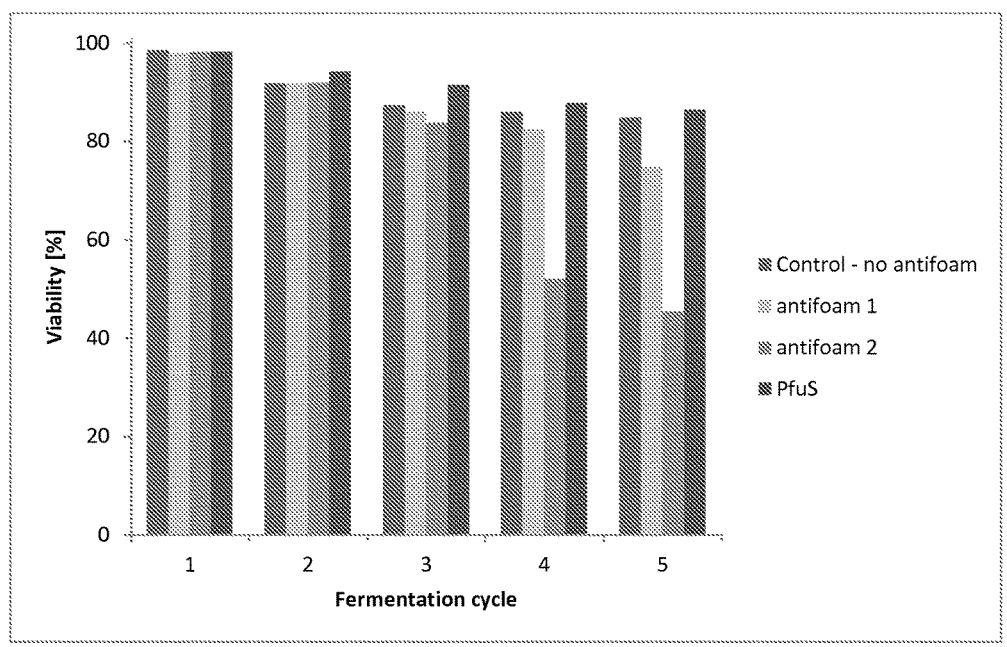
FIG. 4 shows a comparison between the average yeast cell viability [%] of a Control (neither antifoam nor enzyme added), two industrial antifoam agents (antifoam 1 and antifoam 2), and protease PfuS over 5 cycles of fermentation.

FIG. 4 compares the average yeast cell viability of a Control (neither antifoam nor enzyme added), two industrial antifoam agents (antifoam 1 and antifoam 2), and a Protease PfuS over 5 cycles of fermentation. The viability of the yeast was higher for recycled *Saccharomyces cerevisae* yeast in a process of the invention when compared with two commercial antifoam products. Samples treated with industrial antifoam agents showed an increased drop in viability when compared to Control and treatment with protease in accordance with the invention. The inventors also found that when Protease PfuS and Mg Protease 3 were added in cane sugar molasses fermentation no foam was generated. Example 4 shows that certain proteins (likely mannoproteins), release by the yeast cells in the fermentation medium, were degraded. When adding Snapalysin protease and EVERLASE™ protease in synthetic cane sugar molasses fermentation foam was generated and the same proteins (likely mannoproteins) were not hydrolysed. More specifically the invention related to processes of producing a fermentation product from readily fermentable sugar-material, especially sugar cane molasses, in a fermentation vat comprising a fermentation medium using a fermenting organism, comprising:

i) feeding the readily fermentable sugar material into the fermentation vat comprising a slurry of fermenting organism;

ii) fermenting the readily fermentable sugar material into a desired fermentation product, wherein a protease is added a) before, during and/or after feeding in step i), and/or b) during fermentation in step ii).

The fermentation is done with a foaming fermenting organism, such as foaming yeast such as a foaming strain of the genus *Saccharomyces*, such as a foaming strain of *Saccharomyces cerevisiae*. In an embodiment the readily fermentable sugar material is feed into the fermentation vat as a feeding stream. The protease, such as serine protease, especially *Pyrococcus furiosus* protease or a family S53 protease, especially the *Meripilus giganteus* protease 3, may be mixed with the feeding stream of the readily fermentable sugar-material. In a preferred embodiment the protease is mixed with the feeding stream before feeding step i).

According to the invention the term "readily fermentable sugar-material" means that the sugar-containing starting material to be converted/fermented into a desired fermentation product, such as especially ethanol, is of the kind which contains simple sugars, such as sucrose, glucose and fructose, that can be readily fermented by the fermenting organism, such as especially yeast strains derived from *Saccharomyces cerevisae*.

According to the invention the term "fermentation vat" means and includes any type of fermentation vat, fermentation vessel, fermentation tank, or fermentation container, or the like, in which fermentation is carried out.

According to the invention in steps i) and ii) may be carried out simultaneously or sequentially. The fermentation may be carried out at a temperature from 25° C. to 40° C., such as from 28° C. to 35° C., such as from 30° C. to 34° C., preferably around 32° C. In an embodiment the fermentation is ongoing for 2 to 120 hours, in particular 4 to 96 hours. In an embodiment the fermentation may be done in less than 24 hours, such as less than 12 hours, such as between 6 and 12 hours.

In contrast to starch-containing feedstocks, such as corn, wheat, rye, milo, sorghum etc, and cellulosic feedstocks, such corn cobs, corn stover, bagasse, wheat straw, wood etc. there is no need for pretreatment and/or (prior) hydrolysis before fermentation. In a preferred embodiment the readily fermentable sugar-material is selected from the group consisting of sugar cane juice, sugar cane molasses, sweet sorghum, sugar beets, and mixture thereof. However, according to the invention the fermentation medium may also further comprise other by-products of sugar cane, in particular hydrolysate from sugar cane bagasse. In an embodiment the fermentation medium may include separate streams comprising, e.g., C5-liquor, etc. According to the invention the readily fermentable sugar-material (substrate) does not include a substantial content of polysaccharide, such as starch and/or cellulose/hemicellulose.

In a preferred embodiment the fermenting organism used in a process of the invention may be a foaming fermenting organism capable of fermenting readily fermentable sugar-material into a desired fermentation product, such as especially ethanol. Many commercial yeast strains, including especially strains of *Saccharomyces cerevisae*, used commercially, e.g., in Brazil, today, e.g., for producing ethanol from sugar cane molasses generate foam during fermentation. In an embodiment the fermenting organism is a yeast, e.g., from a strain of the genus *Saccharomyces*, such as a strain of *Saccharomyces cerevisiae*. Thus, in a preferred embodiment the fermenting organism is a foaming fermenting organism, such as a foaming strain of *Saccharomyces*, such as especially a strain of *Saccharomyces cerevisae* generating foam during fermentation. According to the invention the density of yeast in the fermentation medium is high, such as from 8-17% w/v, wet basis of the fermentation medium. In an embodiment, the fermentation occurs at non-aseptically conditions, e.g., where wild yeast strains with a foaming phenotype may also be introduced to the fermentation vat and incorporated into the yeast population.

In a preferred embodiment of the invention the fermenting organisms are recycled after fermentation in step ii). According to the invention from 50-100%, such as 70-95%, such as about 90% of the fermentation organisms are recycled. The fermenting organisms, such as yeast, are collected after fermentation in step ii), acid washed, and recycled to the fermentation vat. The fermenting organisms are acid washed with sulfuric acid, e.g., at pH 1.5-3.0, such as 2.0-2.5, e.g., for 1-2 hours. The process of the invention may be carried out as a batch or fed-batch fermentation. However, the process of the invention may also be done as a semi-continuous or continuous process.

The terms "fermentation product" and "desired fermentation product" mean a product produced by fermentation using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. According to the invention the preferred fermentation product is ethanol. The desired fermentation product, such as ethanol, obtained according to the invention, may preferably be used as fuel, e.g., for vehicles, such as cars. Fuel ethanol may be blended with gasoline. Ethanol it may also be used as potable ethanol.

Subsequent to fermentation in step ii) the desired fermentation product, such as ethanol, may be separated from the fermentation medium, e.g., by distillation, or another separation technology. Alternatively, the desired fermentation product may be extracted from the fermentation medium by micro or membrane filtration techniques. The fermentation product may also be recovered by stripping or other method well-known in the art.

Enzymes Addition During Fermentation

A process of the invention, as defined above, includes addition of a protease. In an embodiment the protease is a serine protease capable of cutting protein, such as mannoprotein, on the surface of the foaming fermenting yeast.

In an embodiment the protease is a serine protease capable of cutting cell wall protein, such as mannoprotein, on the surface of the fermenting organism, in particular foaming *Saccharomyces cerevisae* yeast and/or is capable of hydrolyzing protein, such as mannoprotein, in fermented readily fermentable sugar material, such as fermented molasses (wine).

According to an embodiment of the invention the protease may, e.g., be added in a dosage from 0.2 to 25 mg Enzyme Protein (EP)/L fermentation medium.

In an embodiment the protease may be added in dosages from 0.01-100 ppm EP (Enzyme Protein) protease, such as 0.1-50 ppm, such as 1-25 ppm.

The protease used in a process of the invention may preferably be selected from the group of serine proteases, metallo proteases, and aspartic acid proteases. The protease may in one embodiment be the only enzyme added (i.e., no other enzymes added). In a preferred embodiment the protease is of bacterial origin, e.g., a serine protease, such as a bacterial serine protease derived from a strain of *Pyrococcus*, preferably from a strain of *Pyrococcus furiosus*, especially the protease shown in SEQ ID NO: 1 in U.S. Pat. No. 6,358,726 or SEQ ID NO: 2 herein.

The protease may be one having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 2 herein.

In another embodiment the protease used in a process of the invention defined above is of fungal origin.

In another embodiment the protease is a metallo protease. In a preferred embodiment the metallo protease may be derived from a strain of the genus *Thermoascus*, preferably a strain of *Thermoascus aurantiacus*, especially *Thermoascus aurantiacus* CGMCC No. 0670, such as the mature part of SEQ ID NO: 2 disclosed in WO 2003/048353 or SEQ ID NO: 1 herein, or a variant thereof.

In an embodiment the protease or variant thereof has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1.

In another preferred embodiment the protease is a fungal serine protease, such as a serine peptidase family S53 protease ("S53 protease"), such as a family S53 protease derived from a strain of *Meripilus*, preferably a strain of *Meripilus giganteus*. In an embodiment the protease is the mature sequence from *Meripilus giganteus* protease 3 concerned in Example 2 in WO 2014/037438 and shown as SEQ ID NO: 7 herein. In an embodiment the protease is the mature sequence from *Meripilus giganteus* protease 3 shown as SEQ ID NO: 7 herein.

In an embodiment the protease is one having at least 60%, such as at least 70%, such as at least 80%, such as at least 85%, such as at least 90%, such as at least 95%, such as at least 96%, such as at least 97%, such as at least 98%, such as at least 99% identity to SEQ ID NO: 7 herein.

In an embodiment the protease is one having at least 60%, such as at least 70%, such as at least 80%, such as at least 85%, such as at least 90%, such as at least 95%, such as at least 96%, such as at least 97%, such as at least 98%, such as at least 99% identity to SEQ ID: 6 herein.

Examples of suitable proteases can be found in the "Proteases"-section below.

In an embodiment the protease is added together with (simultaneously with) one or more enzymes selected from the group consisting of: cellulase, glucoamylase, alpha-amylase, oxidase, peroxidase, catalase, laccase, beta-glucosidase, other carbohydrases, and oxidases.

In an embodiment the protease is added before and/or after the other enzymes.

According to the process of the invention adding a protease results in increased yields, e.g., ethanol yield, compared to a corresponding process where no protease is present or added. The process of the invention may also reduce the residual sugars present in the fermentation medium. However, most importantly foaming in the fermentation vat is reduced compared to a corresponding process where no protease is added.

According to the invention an alpha-amylase may be added together with the protease or present and/or added during fermentation. The alpha-amylase may be of microbial origin, e.g., fungal or bacterial origin. In an embodiment the alpha-amylase is of fungal origin. In an embodiment the fungal alpha-amylase is derived from a strain of *Rhizomucor*, such as a strain of *Rhizomucor pusillus*, such as a hybrid of the *Rhizomucor pusillus* alpha-amylase shown in SEQ ID NO: 3 herein further comprising a starch-binding module, such as a CBM20 starch-binding module, such as the sequence shown in SEQ ID NO: 4 herein.

In another embodiment the alpha-amylase may be of bacterial origin. In a preferred embodiment the bacterial alpha-amylase may be derived from the genus *Bacillus*, such as a strain of the species *Bacillus stearothermophilus* or variant thereof. The alpha-amylase may be a *Bacillus stearothermophilus* alpha-amylase, e.g., the mature part of the one shown in SEQ ID NO: 5 herein, or a mature alpha-amylase or a corresponding mature alpha-amylase having at least 60%, such as 70%, such as 80% identity, such as at least 90% identity, such as at least 95% identity, such as at least 96% identity, such as at least 97% identity, such as at least 99% identity to the SEQ ID NO: 5 herein. In an embodiment the mature *Bacillus stearothermophilus* alpha-amylase, or variant thereof, is truncated, preferably to have around 485-496 amino acids, scuh as around 491 amino acids. In an embodiment the *Bacillus stearothermophilus* alpha-amylase has a double deletion in positions I181+G182, and optionally a N193F substitution, or deletion of R179+G180 (using SEQ ID NO: 5 herein for numbering).

Examples of suitable alpha-amylase can be found in the "Alpha-Amylases"-section below.

According to the invention a glucoamylase may be added together with the protease or be present and/or added during fermentation. In an embodiment the glucoamylase may be from a strain of *Aspergillus*, preferably *A. niger, A. awamori*, or *A. oryzae*; or a strain of *Trichoderma*, preferably from *Trichoderma reesei*; or a strain of *Talaromyces*, preferably *Talaromyces emersonii*; or a strain of *Trametes*, such as *Trametes cingulate*; or a strain of *Pycnoporus*, or a strain of *Gloephyllum*, or a strain of the *Nigrofomes*.

Examples of suitable glucoamylases can be found in the "Glucoamylases"-section below In an embodiment of the process of the invention a desired fermentation product, such as especially ethanol, is produced from readily fermentable sugar-material by fermentation in a fermentation vat, the process comprises adding protease to the readily fermentable sugar material before feeding; feeding the protease-containing readily fermentable sugar material into the fermentation vat comprising the slurry of fermenting organisms; fermenting the readily fermentable sugar material into the desired fermentation product.

In a preferred embodiment ethanol is produced in a batch or fed-batch fermentation process in a fermentation vat comprising sugar cane molasses, comprising adding protease to the sugar cane molasses before feeding; feeding the protease-containing sugar cane molasses into the fermentation vat comprising a slurry of Saccharomyces cerevisae yeast; and fermenting the sugar cane molasses into ethanol.

In another embodiment a desired fermentation product, such as especially ethanol, is produced from readily fermentable sugar-material by fermentation in a fermentation vat, wherein the process comprises: feeding readily fermentable sugar material into the fermentation vat comprising a slurry of fermenting organisms; feeding protease into the fermentation vat comprising the slurry of readily fermentable sugars and fermenting organisms before fermentation; fermenting the readily fermentable sugar material into the desired fermentation product.

In a preferred embodiment ethanol is produced in a batch or fed-batch fermentation process in a fermentation vat comprising sugar cane molasses, wherein the process comprises: feeding sugar cane molasses into the fermentation vat comprising a slurry of Saccharomyces cerevisae yeast; feeding protease into the fermentation vat comprising the slurry of Saccharomyces cerevisae yeast and the sugar cane molasses before fermentation; fermenting the sugar cane molasses into ethanol.

In a further embodiment of the invention a desired fermentation product is produced from readily fermentable sugar material by fermentation in a fermentation vat, wherein the process comprises: feeding readily fermentable sugar-material into the fermentation vat comprising a slurry of fermenting organisms; adding protease into the fermentation vat during fermentation of the readily fermentable sugar material into the desired fermentation product.

In a preferred embodiment ethanol is produced as a batch or fed-batch fermentation process in a fermentation vat comprising sugar cane molasses, wherein the process comprises: feeding sugar cane molasses into the fermentation vat comprising a slurry of Saccharomyces cerevisae yeast; adding protease into the fermentation vat during fermentation of the sugar cane molasses into ethanol.

In a preferred specific embodiment the process of the invention, comprises
i) feeding the readily fermentable sugar material into the fermentation vat comprising a slurry of fermenting organism;
ii) fermenting the readily fermentable sugar material into a desired fermentation product,
wherein feeding of the readily fermentable sugar-material is done by introducing a feeding stream into the fermentation vat; wherein
protease is mixed with the feeding stream before in step i); or
protease is added to fermentation vat after feeding.

In a preferred embodiment the protease is *Pyrococcus furiosus* protease as described above. In a preferred embodiment the protease is *Meripilus giganteus* protease 3 as described above.

The fermentation is done with a foaming fermenting organism, such as foaming yeast such as a foaming strain of the genus *Saccharomyces*, such as a foaming strain of *Saccharomyces cerevisiae*.

Use of Protease for Foam Reduction

In this aspect the invention relates to the use of a protease for reducing foam generated by fermenting organisms when producing a desired fermentation product from readily fermentable sugars. In a preferred embodiment the desired fermentation product is produced according to a process of the invention.

Enzymes

One or more of the following enzyme activities may be used according to the invention.

Proteases

A process of the invention, as defined above, includes addition of a protease.

The protease may be of any origin. In an embodiment the protease is of fungal origin. In another embodiment the protease is of bacterial origin.

The protease may be a protease selected from the group of serine proteases, metalloproteases, and aspartic acid proteases.

In an embodiment the protease is capable of cutting protein, such as mannoprotein, on the cell wall surface of the foaming fermenting organism, preferably foaming yeast, such as foaming *Saccharomyces cerevisae* yeast. In a preferred embodiment the protease is capable of hydrolyzing protein, in particular mannoprotein, in fermented readily fermentable sugar material, such as fermented molasses (wine).

Fungal Proteases

In an embodiment the protease is of fungal origin.

In a preferred embodiment the protease is a metallo protease, such as one derived from a strain of the genus *Thermoascus*, preferably a strain of *Thermoascus aurantiacus*, especially *Thermoascus aurantiacus* CGMCC No. 0670, or a variant thereof.

In an embodiment the protease, or protease variant, is the metallo protease disclosed as the mature part of SEQ ID NO: 2 disclosed in WO 2003/048353 or SEQ ID NO: 1 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as least 100% identity to the mature part of the polypeptide of SEQ ID NO: 2 disclosed in WO 2003/048353 or SEQ ID NO: 1 herein.

In an embodiment the protease variant has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or SEQ ID NO: 1 herein.

The protease may be a protease variant of the protease shown in SEQ ID NO: 1 herein, having the following substitutions:
D79L+S87P+A112P+D142L
D79L+Y82F+S87P+A112P+D142L
S38T+D79L+S87P+A112P+A126V+D142L D79L+Y82F+S87P+A112P+A126V+D142L
A27K+D79L+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
S70V+D79L+Y82F+S87G+Y97W+A112P+D142L
D79L+Y82F+S87G+Y97W+D104P+A112P+D142L
S70V+D79L+Y82F+S87G+A112P+D142L
D79L+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L
A27K Y82F S87G D104P A112P A126V D142L
A27K D79L Y82F D104P A112P A126V D142L
A27K Y82F D104P A112P A126V D142L In a preferred embodiment the protease is a variant of the *Thermoascus aurantiacus* protease shown in SEQ ID NO: 1 herein with mutations selected from the group consisting of:
A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L.

In an additional embodiment the protease may be a filamentous fungus protease, e.g., derived from a strain of *Rhizomucor*, such as *Rhizomucor miehei*, such as the protease shown in SEQ ID NO: 3 herein, or one having a sequence identity thereto of at least 60%, at least 70%, at least 80%, at least 90%, at least 95%, at least 96%, at least 97%, at least 98%, at least 99%.

In an preferred embodiment the protease is a fungal serine protease, such as a serine peptidase family S53 protease ("S53 protease"), such as a family S53 protease derived from a strain of *Meripilus*, preferably a strain of *Meripilus giganteus*. In an embodiment the family S53 protease is the mature sequence from *Meripilus giganteus* protease 3 concerned in Example 2 in WO 2014/037438 and shown as SEQ ID NO: 7 herein. In an embodiment the protease is the mature sequence from *Meripilus giganteus* protease 3 shown as SEQ ID NO: 6 herein.

In an embodiment the S53 protease is one having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 7 herein.

In an embodiment the S53 protease is one having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 6 herein.

Bacterial Proteases

In an embodiment the protease is of bacterial origin.

In a preferred embodiment the protease is derived from a strain of *Pyrococcus*, preferably a strain of *Pyrococcus furiosus*.

In a preferred embodiment the protease is the one shown in SEQ ID NO: 1 in U.S. Pat. No. 6,258,726 or SEQ ID NO: 2 herein.

In an embodiment the protease has at least 60%, such as at least 70%, such as at least 80%, such as at least 85%, such as at least 90%, such as at least 95%, such as at least 96%, such as at least 97%, such as at least 98%, such as at least 99% sequence identity to SEQ ID NO: 1 in U.S. Pat. No. 6,258,726.

In an embodiment the protease has at least 60%, such as at least 70%, such as at least 80%, such as at least 85%, such as at least 90%, such as at least 95%, such as at least 96%, such as at least 97%, such as at least 98%, such as at least 99% sequence identity to SEQ ID NO: 2 herein.

According to an embodiment of the invention the protease may be added in a dosage from 0.2 to 25 mg Enzyme Protein(EP)/L fermentation medium. In an embodiment the protease may be added in a dosage in the range from 0.01-100 ppm EP (Enzyme Protein) protease, such as 0.1-50 ppm, such as 1-25 ppm.

Alpha-Amylases

According to the invention an alpha-amylase may be added together with the protease or present and/or added during fermentation. The alpha-amylase may be of, e.g., bacterial or fungal origin.

Bacterial Alpha-Amylases

Examples of suitable bacterial alpha-amylases include the below mentioned. Preferred bacterial alpha-amylases may be derived from a strain the genus *Bacillus* (sometimes referred to as *Geobacillus*), including a strain of *Bacillus licheniformis*, *Bacillus amyloliquefaciens*, *Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted I181*+G182*+ N193F) compared to the wild-type BSG alpha-amylase amino acid sequence set forth in SEQ ID NO:3 disclosed in WO 99/19467.

In an embodiment the *Bacillus stearothermophilus* alpha-amylase is one disclosed in WO 2011/082425, or SEQ ID NO: 5 herein, such as one selected from the group of:
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A+Q89R+E129V+K177L+ R179E+Q254S+M284V; and
I181*+G182*+N193F+E129V+K177L+R179E+K220P+ N224L+S242Q+Q254S (using SEQ ID NO: 5 herein for numbering).

In an embodiment the *Bacillus stearothermophilus* alpha-amylase has the following mutations: 181*+G182*+N193F+V59A+Q89R+E129V+K177L+R179E+Q254S+M284V (SEQ ID NO: 5).

The truncated *Bacillus stearothermophilus* alpha-amylase is typically naturally truncated to be about from 485-495 amino acids long, such as 491 amino acids. In a preferred embodiment the truncation is at the C-terminal. A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TERMAMYL™ SC, LIQUOZYME™ SC, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, U.S.A.), FUELZYME™ (Verenium, U.S.A.).

Bacterial alpha-amylase may be added in concentrations well-known in the art. When measured in KNU units (described below in the Materials & Methods"-section) the alpha-amylase activity is preferably present in the range from 0.5-50 KNU/L fermentation medium, such as 1-25 KNU/L fermentation medium, or more preferably in an amount of 2-10 KNU/L fermentation medium.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A./S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication No. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO: 2 herein and SEQ ID NO:100 in U.S. 60/638,614), *Rhizomucor pusillus* alpha-amylase with *Athelia rolfsii* AMG linker and SBD (SEQ ID NO: 3 herein and SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20 SEQ ID NO:72 and SEQ ID NO:96 in U.S. application Ser. No. 11/316,535 and further as SEQ ID NO: 13 herein), and *Meripilus giganteus* alpha-amylase with *Athelia rolfsii* glucoamylase linker and SBD (SEQ ID NO: 4 herein and SEQ ID NO:102 in U.S. 60/638,614). Other specifically contemplated hybrid alpha-amylases are any of the ones listed in Tables 3, 4, 5, and 6 in Example 4 in U.S. application Ser. No. 11/316,535 or (WO 2006/069290) (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

An acid alpha-amylases may be added in an amount of 0.1 to 250 FAU(F)/L fermentation medium, preferably 1 to 100 FAU(F)/L fermentation medium.

Glucoamylase

According to the invention an alpha-amylase may be added together with the protease or present and/or added during fermentation. The alpha-amylase may be of, e.g., bacterial or fungal origin.

Contemplated glucoamylases include those from the group consisting of *Aspergillus* glucoamylases, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot.

Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Pat. No. 7,262,041-B2 (U.S. Ser. No. 10/992,187) (hereby incorporated by reference) or sequences having at least 80% or at least 90% identity thereto.

In a preferred embodiment the glucoamylase is derived from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference.).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME ULTRA, SPIRIZYME EXCEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 1-5,000 AGU/L fermentation medium, preferably 10-1,000 AGU/L fermentation medium.

Materials & Methods
Materials:
Protease PfuS: Protease derived from *Pyrococcus furiosus* shown in SEQ ID NO: 2 herein.
Mg Protease 3: Serine peptidase family S53 protease from a strain of *Meripilus giganteus* concerned in Example 2 in WO 2014/037438.
Protease Z5S17: Purified sample of Snapalysin (Example 4).
Protease Z6Z6A: EVERLASE™ (protease available from Novozymes A/S) (Example 4)
Chemical antifoamer (Examples 1 and 2): AD5520GA (condensed co-polymer from ethylene and propylene oxides) from Alcolina, Brazil.

Antifoam 1: antifoam ART DISP 904 S and dispersant ART DISP 8000, Aratrop Industrial, Brazil (Example 3)
Antifoam 2: antifoam AD4415 and dispersant AD5520GA, Alcolina, Brazil (Example 3)
Yeast (BRT): Brazilian foaming *Saccharomyces cerevisae* strain
Yeast CAT-1: purchased from LNF, Brazil (www.lnf.com.br) and described in Babrzadeh et al., 2012, *"Whole-genome sequencing of the efficient industrial fuel-ethanol fermentative Saccharomyces cerevisiae strain CAT-1"*, Molecular genetics and genomics: MGG 287(6), 485-494.
Substrate: Sugarcane molasses (80° Brix) obtained from Santa Helena mill (Piracicaba, SP, Brazil) (Examples 1 and 2).
Sugar cane molasses samples from São José mill, Brazil (Example 3)
Methods
Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha-amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
|---|---|
| Temperature | 37° C. |
| pH | 4.7 |
| Reaction time | 7-20 minutes |

A detailed description of Novozymes' method for determining KNU and FAU is available on request as standard method EB-SM-0009.02/01.

Determination of acid alpha-amylase activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S). The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 AFAU is defined as the amount of enzyme, which degrades 5.260 mg starch dry matter per hour un-der standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

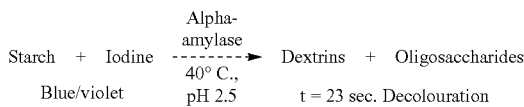

Standard conditions/reaction conditions: (per minute)
Substrate: starch, approx. 0.17 g/L
Buffer: Citrate, approx. 0.03 M
Iodine ($I_2$): 0.03 g/L
$CaCl_2$: 1.85 mM
pH: 2.50+/−0.05
Incubation temperature: 40° C.
Reaction time:
Wavelength: Lambda=590 nm
Enzyme concentration: 0.025 AFAU/mL
Enzyme working range: 0.01-0.04 AFAU/mL Further details can be found in standard method document EB-SM-0259.02/01 available on request from Novozymes A/S, which folder is hereby incorporated by reference.

Determination of FAU(F)

FAU(F) Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e. 25° C., pH 5.5 and 10 min. reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assays

AZCL-Casein Assay

A solution of 0.2% of the blue substrate AZCL-casein is suspended in Borax/$NaH_2PO_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Comparison Between Chemical Antifoamer and PfuS Protease on Foam Control in Sugarcane Molasses Fermentation Fermentation trials were performed at 32° C. in 50 mL centrifuge vials (TPP), simulating an industrial ethanol fermentation process as performed in Brazil. A foaming Brazilian yeast strain was used. A fermentation substrate containing 22° Brix (composed of diluted molasses) was fed into a yeast slurry (prepared by resuspending acid treated yeast biomass in water). The yeast slurry represented 30% of the total fermentation volume, similar to industrial conditions. After fermentation for around 6 hours, yeast cells were collected by centrifugation (4000 rpm for 10 min), weighed, diluted with fermented molasses (wine) and water (to 35% w/v yeast wet weight), and treated with sulfuric acid (pH from 2.0 to 2.5 for 1 hour) and reused in subsequent 9 fermentation cycles. Samples were run in triplicate at each condition. Wet weight yeast biomass was determined gravimetrically after centrifugation (4000 rpm for 10 min) of the samples. Foam was registered every hour after feeding by recording the foam height in tubes and/or by taking pictures of representative 50 mL tubes. Conditions were:

control—no enzyme. No Chemical antifoamer was added during acid wash.

chemical antifoamer addition. Chemical antifoamer was added during acid wash, with increasing dosages after each cycle, until foam was controlled.

Protease PfuS addition. Protease PfuS was added after new molasses was added. No Chemical antifoamer was added during acid wash.

The dosages used were according Table 1. Antifoamer was added in the yeast slurry. Protease PfuS was added after the fermentation vat was fed with fresh molasses.

TABLE 1

Dosages of antifoam oil and PfuS used for controlling foaming

| Product | Concentration (mg/L) |
|---|---|
| Chemical antifoamer | 10 to 30 |
| PfuS Protease | 3.7 and 7.5 |

Foam measurements resulted in the following data, showing the more significant results, summarized in Table 2:

TABLE 2

Foam control results from each treatment. Data are presented on total volume increase compared to medium volume, due to foam formation.

| Treatment | Total volume increase (foam formation) |
|---|---|
| Control | +94% |
| Chemical AntifoamerI (10 ppm) | +94% |
| Chemical AntifoamerI (20 ppm) | +29% |
| Chemical Antifoamer (30 ppm) | +23% |
| Protease PfuS (3.7 ppm) | +8% |
| Protease PfuS (7.5 ppm) | +0% |

After Chemical antifoamer and Protease PfuS addition had ceased, the foam height was measured in the next three subsequent fermentation cycles. Tubes where Protease PfuS had been added presented a residual antifoam effect on the two sequential batches after last Protease PfuS addition. Foam formation, presented in total volume increase, is summarized in Table 3:

TABLE 3

Foam formation in two batches (cycle 1 and cycle 2) after Antifoam oil and Protease PfuS addition had ceased. Data are presented on total volume increase compared to medium volume, due to foam formation.

| Treatment | Cycle 1 | Cycle 2 |
|---|---|---|
| Control | +100% | +101% |
| Chemical Antifoamer | +98% | +101% |
| Protease PfuS (3.7 ppm) | +17% | +13% |
| Protease PfuS (7.5 ppm) | +10% | +24% |
| Protease PfuS (3.7 ppm, single addition)* | +11% | +21% |

*A single dosage of Protease PfuS (3.7 ppm) was added to this tube and its foam was measured up to three cycles after single dosage addition.

Example 2

Protease PfuS Effect on Yeast Biomass Production and Viability Maintenance in Sugarcane Molasses Fermentation, Using a Cell Recycle System Fermentation trials were performed at 32° C. in 50 mL centrifuge vials (TPP), simulating an industrial ethanol fermentation process as performed in Brazil. The same native foaming Brazilian yeast strain used in Example 1 was used. A fermentation substrate containing 22° Brix (diluted molasses) was fed into a yeast slurry (prepared by resuspending acid treated yeast biomass in water). The yeast slurry represented 30% of the total fermentation volume, similar to industrial conditions. After fermentation, yeast cells were collected by centrifugation (4000 rpm for 10 min), weighed, diluted with fermented molasses (wine) and water (to 35% w/v yeast wet weight), and treated with sulfuric acid (pH from 2.0 to 2.5 for 1 hour) and reused in subsequent 9 fermentation cycles. Samples were run in triplicate at each condition. Wet weight yeast biomass was determined gravimetrically after centrifugation (4000 rpm for 10 min) of the samples. After yeast biomass centrifugation, wines had their pHs determined by the end of each cycle. The yeast viability was assayed by microscopically cell count, with erythrosine red dye.

Conditions were:

control—no enzyme; No Chemical antifoamer was added during acid wash.

Protease PfuS addition. Protease PfuS was added after new molasses was added. No Chemical antifoamer was added during acid wash.

The dosages were according Table 1. Protease PfuS was added after the vat was fed with fresh molasses.

TABLE 1

Protease dosage addition for each treatment.

| Treatment | Protease dosage (mg/L) |
| --- | --- |
| Control | 0 |
| Protease PfuS 2.5 ppm | 2.5 to 1.9 |
| Protease PfuS 5 ppm | 5 to 3.7 |
| Protease PfuS 10 ppm | 10 to 7.5 |

Figure 1:
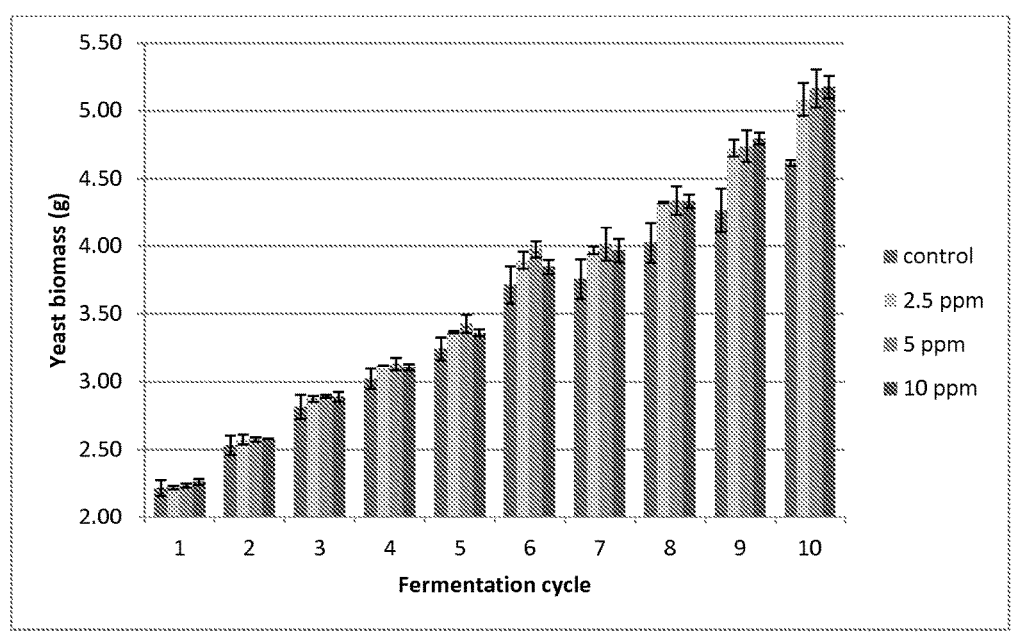
FIG. 1 shows a comparison between the average biomass in the Control (no enzyme addition) and the average biomass of protease treated samples (2.5, 5 and 10 ppm; 1.9, 3.7 and 7.5 ppm on cycles 9 and 10) along with 9 cycles of fermentation. Point 10 was taken after last fermentation batch.

During the experiment, yeast biomass (wet basis) measurements for each treatment showed a significant increase in treated samples, when compared to the Control, as depicted on FIG. 1:

FIG. 1 shows a comparison between the average yeast biomass of a Control (no enzyme addition) and the average yeast biomass of treated samples (2.5 ppm, 5 ppm and 10 ppm; 1.9 ppm, 3.7 ppm and 7.5 ppm in cycles 9 and 10) over 9 cycles of fermentation. Point 10 was taken after last fermentation batch. As can be seen from FIG. 1, for treated samples the average increase in yeast biomass is about 12% when compared to the Control. Viability results are presented in FIG. 2.

Figure 2:
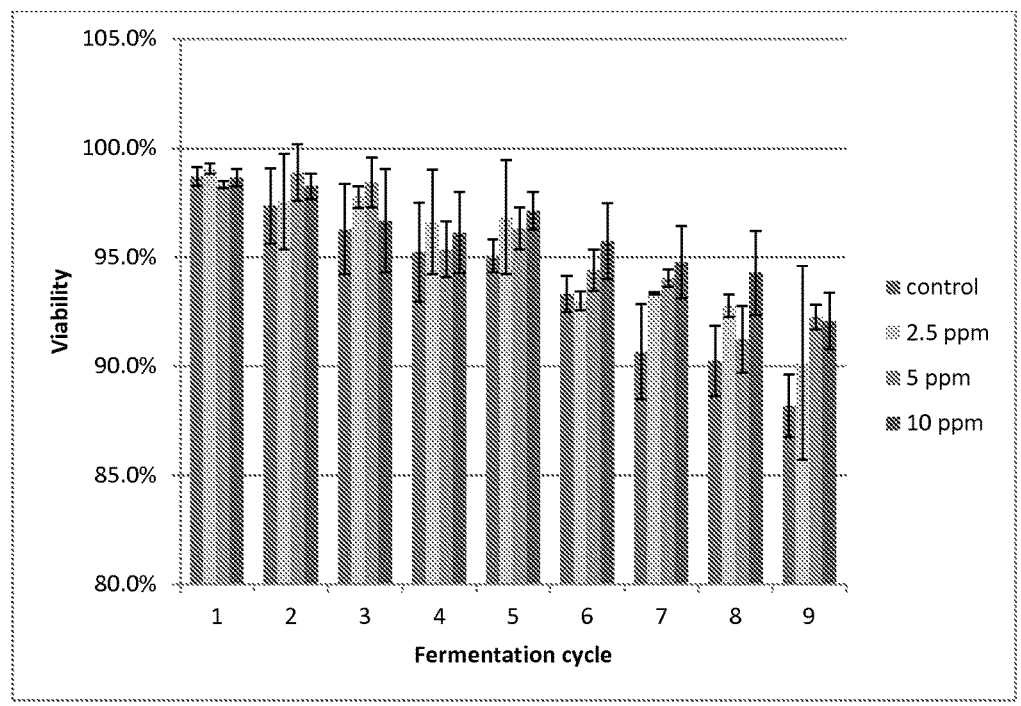
FIG. 2 shows a comparison between the average viability in the Control (no enzyme addition) samples and the average viability of treated samples (2.5, 5 and 10 ppm; 1.9, 3.7 and 7.5 ppm on cycles 9 and 10) along 9 cycles of fermentation.

FIG. 2 shows a comparison between the average yeast viability of a Control (no enzyme addition) and the average yeast viability of treated samples (2.5 ppm, 5 ppm and 10 ppm; 1.9 ppm, 3.7 ppm and 7.5 ppm in cycles 9 and 10) over 9 fermentation cycles. Treated samples with higher protease dosage (i.e. 3.7 ppm to 10 ppm) resulted in an average of 5% more viable cells than the Control after 9 sequential fermentation cycles.

Example 3

Ethanol Productivity and Viability Effect of Chemical Antifoams and Protease

Fed-batch fermentations, simulating an industrial fuel ethanol fermentation process as performed in Brazil, were carried out in 50 mL falcon tubes. A non-foaming yeast strain CAT-1 (*Saccharomyces cerevisae* yeast) was used. For the first cycle, yeast cells from the propagation culture were added to each tube in an amount corresponding to 8% (w/v) of the final volume. Cells were fed with 25 mL sugar cane must (sugar cane molasses diluted to 20 Brix in (Brazilian) tap water, centrifuged to remove solids, and autoclaved) in three equal sized portions with 1.5 hours interval. Cultures were incubated for 7 hours at 32° C. without agitation and left at room temperature overnight. The following day, cells were separated from the fermentation wine by centrifugation (3220 rcf, 5 min) and re-suspended in wine [30% (wet w/w)] to simulate the industrial centrifuge efficiency. Cells were further diluted in demineralized water (1:1) before addition of 1 M sulphuric acid to a final pH of 2.5. After incubation in acid at room temperature for 1 hour, feeding was initiated restarting the process.

Industrial antifoam 1 (antifoam ART DISP 904 S and dispersant ART DISP 8000, Aratrop Industrial, Brazil) and antifoam 2 (antifoam AD4415 and dispersant AD5520GA, Alcolina, Brazil) were administered as in the industry, with the dispersant added during the acid wash and antifoam after 1 hour of fermentation. PfuS was added straight to the feeding medium in a concentration of 5 ppm EP (Enzyme Protein).

Samples from sugar cane fermentations were diluted 1000 times in milliQ water to a final concentration of approximately 500 cells/mL. Cells were were dyed with propidium iodide (PI) (215 nmol/mL) and incubated for 5-10 min in the dark before applying the samples on a flow cytometer (BD accuri C6) according to the manufacturers recommendations. Threshold of FSC-H gate was set to 200,000 to avoid large particles. Quantification of viability was done by separating two populations generated from the histogram of the PI fluorophore detector FL3-H. Fermentation kinetics was also monitored by weighing the tubes hourly. Considering that cumulative $CO_2$ evolution is proportional to ethanol formation at a rate of ~1:1 in terms of moles, it is possible to infer ethanol cumulative evolution, which is directly correlated to ethanol productivity (g ethanol·L−1·h−1).

Ethanol productivity was monitored throughout all fermentation cycles and used as a measure for metabolic activity and ethanol formation. FIG. 3 shows a comparison between the average ethanol productivity of a control (neither antifoam nor enzyme added), two industrial antifoam agents (antifoam 1 and antifoam 2), and protease PfuS over 5 cycles of fermentation. Samples treated with industrial antifoam agents showed less ethanol productivity than the control and treatment with protease.

Another important parameter of the fermentations was the viability which was monitored after each cycle. FIG. 4 shows a comparison between the average yeast cell viability of a control (neither antifoam nor enzyme added), two industrial antifoam agents (antifoam 1 and antifoam 2), and a protease (PfuS) over 5 cycles of fermentation. Samples treated with industrial antifoam agents showed an increased drop in viability when compared to control and treatment with protease.

Example 4

Effect of Protease Addition to Protein Levels in Foaming-Yeast Fermentation

Fed-batch fermentation, simulating an industrial fuel ethanol fermentation process as performed in Brazil, were carried out in 50 mL falcon tubes. A foaming Brazilian yeast strain (BRT) was used (*Saccharomyces cerevisae* yeast) and compared to a non-foaming yeast (CAT-1. Yeast cells were added to each tube in an amount corresponding to 10% (w/v) of the final volume. Cells were fed with an adequate volume of chemically defined media (YNB media without amino acids and 10 mM citrate buffer pH 5.5; Sigma-Aldrich), with glucose as the sole carbon source (16% w/v). Cultures were incubated for 7 hours at 32° C. without agitation and left at room temperature overnight. The following day, cells were separated from the fermentation wine by centrifugation (3220 rcf, 10 min) and re-suspended in wine [30% (wet w/w)] to simulate the industrial centrifuge efficiency. Cells were further diluted in demineralized water (1:1). After that dilution, fresh media was added to the slurry and the process was started all over again. Protease was added to treatment tubes at a concentration of 10 ppm (10 mg EP/L). Control tubes received no enzyme.

Protein Precipitation with TCA Solution

Wines from the above fermentation set up were initially pooled together and filtered in 0.22 μm. Samples from each pool were collected and 0.11 volumes of ice-cold 100% TCA solution were added for protein precipitation. Tubes were placed on ice for 10 min and after that 0.500 mL of ice-cold 10% TCA was added to the sample. Tubes were placed on ice for additional 20 min and centrifuged at 20,000 g for 30 min. Supernatant was removed and 0.500 mL of acetone was added to the pellet. Tubes were gently rocked and centrifuged at 20,000 g for 10 min. Supernatant was removed. Pellets were left for 15 minutes to dry.

SDS-PAGE Gel Electrophoresis

Protein pellets from TCA precipitation were re-suspended directly into Laemmli loading buffer (according to the manufacturer's instruction) for SDS-PAGE analysis. Samples were then heated at 100° C. for 5 minutes on a heat block. 45 µL of each sample was injected in separate wells of the gel (Criterion TGX Stain-Free 4-20%, 12 wells). 0.010 mL of the marker (Bio-Rad Precision Plus Protein Unstained Standard) were added to a separate well. Gel was run at 120V (constant voltage) for approximately 1 hour. The gel was transferred to a Bio-Rad Stain-Free Sample Tray and analyzed on a Gel Doc EZ Imager, using the ImageLab software.

Figure 5:
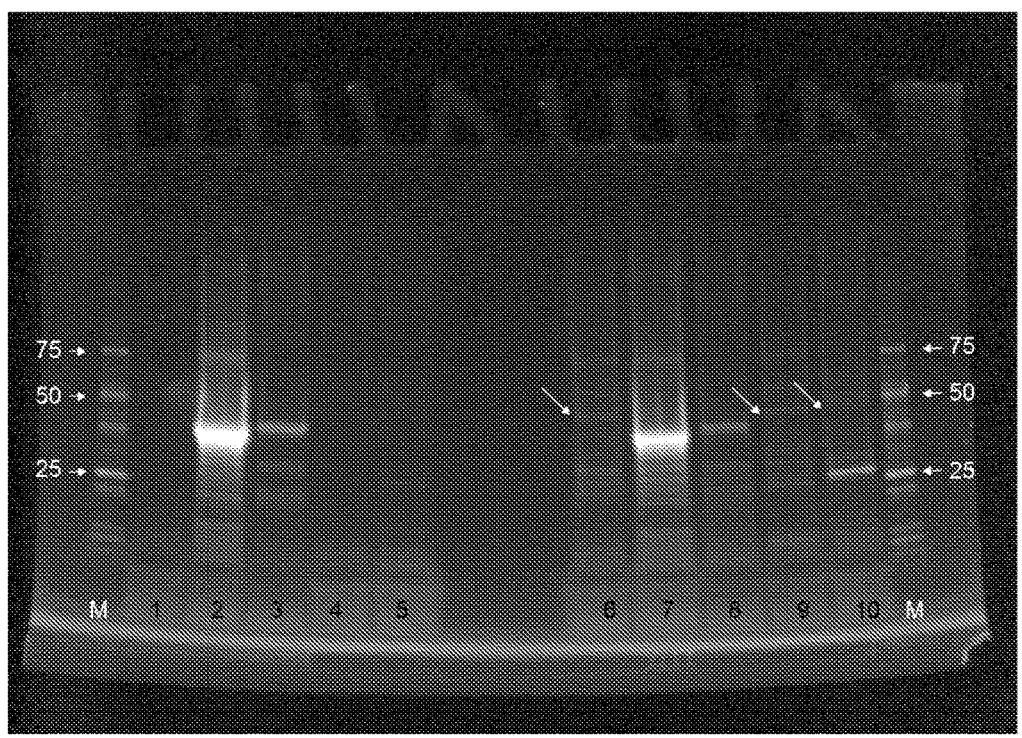
FIG. 5 shows a SDS-PAGE analysis of protein fragments from foaming yeast (BRT) and non-foaming yeast (CAT-1) fermentation supernatants (wines), treated with different proteases. Markers are shown as Kda and some protein fragments are indicated by arrows. The lanes are as follows.

A photo of the SDS-Page gel is shown in FIG. 5

| Lane# | Description Yeast/enzyme/medium | Foam control |
|---|---|---|
| 1 | CAT-1, control wine | No foam |
| 2 | CAT-1, Protease PfuS treated wine | No foam |
| 3 | CAT-1, Mg Prot 3 treated wine | No foam |
| 4 | CAT-1, Protease Z5S17 treated wine | No foam |
| 5 | CAT-1, Protease Z6Z6A treated wine | No foam |
| 6 | BRT, control wine | Foam |
| 7 | BRT, Protease PfuS treated wine | No foam |
| 8 | BRT, Mg Prot 3 treated wine | No foam |
| 9 | BRT, Protease Z5S17 treated wine | Foam |
| 10 | BRT, Protease Z6Z6A treated wine, | Foam |

CONCLUSION

Foaming yeast strain (BRT) releases significantly more protein fragments into the fermenting media (wine) when compared to non-foaming strain (CAT-1).

The Protease PfuS and Mg Prot 3 degrade one of these protein bands (indicated by the arrow in FIG. 5), while the other two proteases (Protease Z5S17 and Protease Z6Z6A) that do not control foam are not able to degrade this band (see band in the range of 25-50 KDa).

REFERENCES

Cold Spring Harb Protoc; 2011; doi:10.1101/pdb.prot5651
Adapted from Proteomics: A Cold Spring Harbor Laboratory Course Manual, by Andrew J. Link and Joshua LaBaer. CSHL Press, Cold Spring Harbor, N.Y., U.S.A., 2009.

SUMMARY PARAGRAPHS

The present invention is defined in the claims and accompanying description. For convenience, other aspects of the present invention are presented herein by way of numbered paragraphs:

1. A process of producing a fermentation product from readily fermentable sugar-material in a fermentation vat comprising a fermentation medium using a fermenting organism, comprising
    i) feeding the readily fermentable sugar material into the fermentation vat comprising a slurry of fermenting organism;
    ii) fermenting the readily fermentable sugar material into a desired fermentation product,
    wherein a protease is added
        a) before, during and/or after feeding in step i), and/or
        b) during fermentation in step ii).
2. The process of paragraph 1, wherein the readily fermentable sugar material is feed into the fermentation vat as a feeding stream.
3. The process of paragraph 2, wherein the protease is mixed with the feeding stream of the readily fermentable sugar-material.
4. The process of paragraph 3, wherein the protease is mixed with the feeding stream of readily fermentable sugar-material before feeding step i).
5. The process of any of paragraphs paragraphs 1-4, wherein the readily fermentable sugars-material is selected from the group consisting of sugar cane juice, sugar cane molasses, sweet sorghum, sugar beets, and mixture thereof.
6. The process of any of paragraphs 1-5, wherein the fermentation medium further comprises other by-products of sugar cane, in particular hydrolysate from sugar cane bagasse and its streams.
7. The process of any one of paragraphs 1-6, wherein the fermenting organism is a yeast, foaming yeast, e.g., from a strain of the genus *Saccharomyces*, such as a strain of *Saccharomyces cerevisiae*, especially a strain of *Saccharomyces cerevisae* generating foam when fermented.
8. The process of any of paragraphs 1-7, wherein the fermenting organisms are recycled after fermentation in step ii).
9. The process of paragraph 8, wherein from 50-100%, such as 70-95%, such as about 90% of the fermentation organisms are recycled.
10. The process of any of paragraphs 1-9, wherein the fermentation organism cell densities during fermentation is 8-17% w/v (wet basis).
11. The process of any of paragraphs 9 or 10, wherein the fermenting organisms, such as yeast, are collected after fermentation in step ii), acid washed, and recycled to the fermentation vat.
12. The process of paragraph 11, wherein fermenting organisms, such as yeast, are collected after fermentation in step ii), and acid washed with sulfuric acid, e.g., at pH 1.5-3.0, such as 2.0-2.5, e.g., for 1-2 hours.
13. The process of any of paragraphs 1-12, wherein the fermentation is carried out as batch, fed-batch or continuous fermentation.
14. The process of any of paragraphs 1-13, wherein the fermentation product is an alcohol, preferably ethanol, especially fuel ethanol, potable ethanol and/or industrial ethanol.
15. The process of any of paragraphs 1-14, wherein the protease is added in a dosage of 0.2 to 25 mg Enzyme Protein/L fermentation medium or 0.01-100 ppm EP (Enzyme Protein), such as 0.1-50 ppm EP, in particular 1-25 ppm EP.
16. The process of any of paragraphs 1-15, wherein the protease is the only enzyme added.
17. The process of any of paragraphs 1-16, wherein the protease is added together with one or more enzymes selected from the group consisting of: cellulase, glucoamylase, alpha-amylase, oxidase, peroxidase, catalase, laccase, beta-glucosidase, other carbohydrases, and oxidases.
18. The process of any of paragraphs 1-17, wherein foaming in the fermentation vat is reduced compared to a corresponding process where no protease is added.
19. The process of paragraph 18, wherein the protease is added after the other enzymes, preferably one or more of the enzymes in paragraph 17.

20. The process of any of paragraph 1-19, wherein adding protease result in increased yields, e.g., ethanol yield, compared to a corresponding process where no protease is present or added.

21. The process of any of paragraphs 1-20, wherein the the residual sugars present in the fermentation medium is reduced.

22. The process of any of paragraphs 1-21, wherein step i) and ii) are carried out simultaneously or sequentially.

23. The process of any of paragraphs 1-22, wherein fermentation is carried out at a temperature from 25° C. to 40° C., such as from 28° C. to 35° C., such as from 30° C. to 34° C., preferably around about 32° C.

24. The process of any of paragraphs 1-23, wherein fermentation is ongoing for 2 to 120 hours, in particular 4 to 96 hours, such as between 6 and 12 hours.

25. The process of any of paragraphs 1-24, wherein the fermentation product is recovered after fermentation, such as by distillation.

26. The process of any of paragraphs 1-25, wherein the protease is selected from the group of serine proteases, metalloproteases, and aspartic acid proteases.

27. The process of any of paragraphs 1-26, wherein the protease is capable of cutting cell wall protein, in particular mannoprotein, on the surface of the fermenting organism, in particular *Saccharomyces cerevisae* yeast and/or is capable of hydrolyzing protein, in particular mannoprotain, in fermented readily fermentable sugar material such as fermented molasses (wine).

28. The process of any of paragraphs 1-27, wherein the protease of microbial origin, e.g., fungal or bacterial origin.

29. The process of any of paragraphs 1-28, wherein the protease is of fungal origin.

30. The process of any of paragraphs 1-29, wherein the protease is a metallo protease, such as one derived from a strain of the genus *Thermoascus*, preferably a strain of *Thermoascus aurantiacus*, especially *Thermoascus aurantiacus* CGMCC No. 0670, such as the mature part of SEQ ID NO: 2 disclosed in WO 2003/048353 or the mature part of SEQ ID NO: 1 in WO 2010/008841 or SEQ ID NO: 1 herein, or a variant thereof.

31. The process of any of paragraphs 1-30, wherein the protease or variant thereof has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1.

32. The process of any of paragraphs 1-31, wherein the protease is of bacterial origin.

33. The process of any of paragraphs 1-32 wherein the protease is a serine protease, such as a protease derived from a strain of *Pyrococcus*, preferably a strain of *Pyrococcus furiosus*.

34. The process of any of paragraphs 1-33, wherein the protease is the one shown in SEQ ID NO: 1 in U.S. Pat. No. 6,358,726 or SEQ ID NO: 2 herein.

35. The process of any of paragraphs 1-34, wherein the protease is one having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 2 herein.

36. The process of any of paragraphs 1-35, wherein the protease is a serine protease, such as a serine peptidase family S53 protease, such as a S53 protease derived from a strain of *Meripilus*, preferably a strain of *Meripilus giganteus*.

37. The process of any of paragraphs 1-36, wherein the protease is the mature sequence from *Meripilus giganteus* protease 3 from example 2 in WO 2014/037438 or SEQ ID NO: 6 herein or SEQ ID NO: 7 herein.

38. The process of any of paragraphs 1-37, wherein the protease is one having at least 60%, such as at least 70%, such as at least 80%, such as at least 85%, such as at least 90%, such as at least 95%, such as at least 96%, such as at least 97%, such as at least 98%, such as at least 99% identity to in SEQ ID NO: 6 herein or SEQ ID NO: 7 herein.

39. The process of any of paragraphs 1-38, further wherein an alpha-amylase may be added together with the protease or present and/or added during fermentation.

40. The process of paragraph 39, wherein the alpha-amylase is of microbial origin, e.g., fungal or bacterial origin.

41. The process of paragraph 40, wherein the alpha-amylase is of fungal origin.

42. The process of paragraph 41, wherein the fungal alpha-amylase is derived from a strain of *Rhizomucor*, such as a strain of *Rhizomucor pusillus*, such as a hybrid of the *Rhizomucor pusillus* alpha-amylase shown in SEQ ID NO: 3 further comprising a starch-binding module, such as a CBM20 starch-binding module, such as the sequence shown in SEQ ID NO: 4.

43. The process of paragraph 42, wherein the alpha-amylase is of bacterial origin.

44. The process of paragraph 43, wherein the bacterial alpha-amylase is derived from the genus *Bacillus*, such as a strain of the species *Bacillus stearothermophilu*, or variant thereof.

45. The process of paragraph 44, wherein the alpha-amylase is a mature *Bacillus stearothermophilus* alpha-amylase or corresponding mature alpha-amylases having at least 60%, such as at least 70%, such as at least 80% identity, such as at least 90% identity, such as at least 95% identity, such as at least 96% identity, such as at least 97% identity, such as at least 99% identity to SEQ ID NO: 5 herein.

46. The process of paragraph 44 or 45, wherein the mature *Bacillus stearothermophilus* alpha-amylase, or variant thereof, is truncated, preferably to have around 485-496 amino acids, such as around 491 amino acids 47. The process of any of paragraphs 44-46, wherein the *Bacillus stearothermophilus* alpha-amylase has a double deletion in positions I181+G182, and optionally a N193F substitution, or deletion of R179+G180 (using SEQ ID NO: 5 herein for numbering).

48. The process of any of paragraphs 1-47, further wherein a glucoamylase is added together with the protease or be present and/or added during fermentation.

49. The process of paragraph 48, wherein the glucoamylase is a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Trametes*, such as *Trametes cingulate*, or a strain of *Pycnoporus*, or a strain of *Gloephyllum*, or a strain of the *Nigrofomes*.

50. The process of any of paragraphs 1-49, wherein the readily fermentable sugar-material substrate is not containing polysaccharide, such as starch and/or cellulose/hemicellulose.

51. The process of any of paragraphs 1-50, wherein the desired fermentation product is produced from readily fermentable sugar material by fermentation in a fermentation vat, the process comprises adding protease to the readily fermentable sugar material before feeding; feeding the protease-containing readily fermentable sugar material into the fermentation vat comprising a slurry of fermenting organisms; fermenting the readily fermentable sugar material into the desired fermentation product.

52. The process of any of paragraphs 1-51, wherein ethanol is produced in a batch, fed batch, semi-continuous or continuous fermentation process in a fermentation vat comprising sugar cane molasses, comprising adding protease to the sugar cane molasses before feeding; feeding the protease-containing sugar cane molasses into the fermentation vat comprising a slurry of *Saccharomyces cerevisae* yeast; and fermenting the sugar cane molasses into ethanol.

53. The process of any of paragraphs 1-52, wherein ethanol is produced from sugar cane molasses by fermentation in a fermentation vat, the process comprises adding *Pyrococcus furiosus* protease to the sugar cane molasses before feeding; feeding the *Pyrococcus furiosus* protease-containing sugar cane molasses into the fermentation vat comprising a slurry of *Saccharomyces cerevisae* yeast; fermenting the sugar cane molasses into ethanol.

54. The process of any of paragraphs 1-53, wherein ethanol is produced from sugar cane molasses by fermentation in a fermentation vat, the process comprises adding a peptidase family S53 protease, in particular *Meripilus giganteus* protease 3 to the sugar cane molasses before feeding; feeding peptidase family S53 protease, in particular *Meripilus giganteus* protease 3, containing sugar cane molasses into the fermentation vat comprising a slurry of *Saccharomyces cerevisae* yeast; fermenting the sugar cane molasses into ethanol.

55. The process of any of paragraphs 1-54, wherein the desired fermentation product is produced from readily fermentable sugar material by fermentation in a fermentation vat, wherein the process comprises: feeding readily fermentable sugar material into the fermentation vat comprising a slurry of fermenting organisms; feeding protease into the fermentation vat comprising a slurry of readily fermentable sugars and fermenting organisms before fermentation; fermenting the readily fermentable sugar material into the desired fermentation product.

56. The process of any of paragraphs 1-55, wherein ethanol is produced in a batch or fed batch fermentation process in a fermentation vat comprising sugar cane molasses, wherein the process comprises: feeding sugar cane molasses into the fermentation vat comprising a slurry of *Saccharomyces cerevisae* yeast; feeding protease, preferably serine protease, into the fermentation vat comprising a slurry of *Saccharomyces cerevisae* yeast and the sugar cane molasses before fermentation; fermenting the sugar cane molasses into ethanol.

57. The process of any of paragraphs 1-56, wherein ethanol is produced from sugar cane molasses by fermentation in a fermentation vat, wherein the process comprises: feeding sugar cane molasses into the fermentation vat comprising a slurry of fermenting organisms; feeding *Pyrococcus furiosus* protease into the fermentation vat comprising a slurry of sugar cane molasses and *Saccharomyces cerevisae* yeast before fermentation; fermenting the sugar cane molasses into ethanol.

58. The process of any of paragraphs 1-57, wherein ethanol is produced from sugar cane molasses by fermentation in a fermentation vat, wherein the process comprises: feeding sugar cane molasses into the fermentation vat comprising a slurry of fermenting organisms; feeding a peptidase family S53 protease, in particular *Meripilus giganteus* protease 3, into the fermentation vat comprising a slurry of sugar cane molasses and *Saccharomyces cerevisae* yeast before fermentation; fermenting the sugar cane molasses into ethanol.

59. The process of any of paragraphs 1-58, wherein the desired fermentation product is produced from readily fermentable sugar material by fermentation in a fermentation vat, wherein the process comprises: feeding readily fermentable sugar material into the fermentation vat comprising a slurry of fermenting organisms; adding protease into the fermentation vat during fermentation of the readily fermentable sugar-material into the desired fermentation product.

60. The process of any of paragraphs 1-59, wherein ethanol is produced as a batch, fed batch, semi-continuous or continuous fermentation process in a fermentation vat comprising sugar cane molasses, wherein the process comprises: feeding sugar cane molasses into the fermentation vat comprising a slurry of *Saccharomyces cerevisae* yeast; adding protease, in particular serine protease, into the fermentation vat during fermentation of the sugar cane molasses into ethanol.

61. The process of any of paragraphs 1-60, wherein ethanol is produced from sugar cane molasses by fermentation in a fermentation vat, wherein the process comprises: feeding sugar cane molasses into the fermentation vat comprising a slurry of *Saccharomyces cerevisae* yeast; adding *Pyrococcus furiosus* protease into the fermentation vat during fermentation of the sugar cane molasses into ethanol.

62. The process of any of paragraphs 1-61, wherein ethanol is produced from sugar cane molasses by fermentation in a fermentation vat, wherein the process comprises: feeding sugar cane molasses into the fermentation vat comprising a slurry of *Saccharomyces cerevisae* yeast; adding a peptidase family S53 protease, in particular *Meripilus giganteus* protease 3, into the fermentation vat during fermentation of the sugar cane molasses into ethanol.

63. The process of any of paragraphs 1-62, comprising i) feeding the readily fermentable sugar material into the fermentation vat comprising a slurry of fermenting organism;

ii) fermenting the readily fermentable sugar material into a desired fermentation product, wherein feeding of the readily fermentable sugar-material is done by introducing a feeding stream into the fermentation vat; wherein protease is mixed with the feeding stream before in step i); or protease is added to fermentation vat after feeding.

64. The process of paragraph 63, wherein the protease is *Pyrococcus furiosus* protease.

65. The process of paragraph 63, wherein the protease is *Meripilus giganteus* protease 3.

66. Use of a protease for reducing foam generated by fermenting organisms when producing a desired fermentation product from readily fermentable sugars.

67. The use according to paragraph 66, wherein the desired fermentation product is produced as defined in any of paragraphs 1-65.

The invention claimed is:

1. A process of producing a fermentation product from readily fermentable sugar-material in a fermentation vat comprising a fermentation medium using a fermenting organism, the method comprising:
   i) feeding the readily fermentable sugar material into the fermentation vat comprising a slurry of fermenting organism;
   ii) fermenting the readily fermentable sugar material into a desired fermentation product,
   wherein a protease is added
   a) before, during and/or after feeding in step i), and/or
   b) during fermentation in step ii);
   wherein the fermentation product is ethanol;
   wherein the readily fermentable sugar-material comprises sugar cane juice, sugar cane molasses, sweet sorghum or sugar beets;
   wherein the fermenting organism is *Saccharomyces cerevisiae*; and
   wherein the protease is the *Pyrocuccus furiousus* protease of SEQ ID NO: 2, or a protease having at least 95% sequence identity to the protease of SEQ ID NO: 2; or the *Meripilus giganteus* protease of SEQ ID NO: 7, or a protease having at least 95% sequence identity to the protease of SEQ ID NO: 7.

2. The process of claim 1, wherein the readily fermentable sugar material is feed into the fermentation vat as a feeding stream.

3. The process of claim 2, wherein the protease is mixed with the feeding stream of the readily fermentable sugar-material.

4. The process of claim 1, wherein the protease is mixed with the feeding stream of readily fermentable sugar-material before feeding step i).

5. The process of claim 1, wherein the fermenting organism is a strain of *Saccharomyces cerevisae* generating foam when fermented.

6. The process of claim 1, wherein the fermenting organism is recycled after fermentation in step ii).

7. The process of claim 5, wherein the fermenting organism is collected after fermentation in step ii), acid washed, and recycled to the fermentation vat.

8. The process of claim 1, wherein the readily fermentable sugar-material substrate does not contain starch or cellulose/hemicellulose.

9. The process of claim 1, wherein the fermentation product is produced from readily fermentable sugar material by fermentation in a fermentation vat, the process comprising adding the protease to the readily fermentable sugar material before feeding; feeding the protease-containing readily fermentable sugar material into the fermentation vat comprising a slurry of fermenting organism; and fermenting the readily fermentable sugar material into the fermentation product.

10. The process of claim 1, wherein ethanol is produced in a batch, fed batch, semi-continuous or continuous fermentation process in a fermentation vat comprising sugar cane molasses, comprising adding the protease to the sugar cane molasses before feeding; feeding the protease-containing sugar cane molasses into the fermentation vat comprising a slurry of *Saccharomyces cerevisae* yeast; and fermenting the sugar cane molasses into ethanol.

11. The process of claim 1, wherein the fermentation product is produced from readily fermentable sugar material by fermentation in a fermentation vat, wherein the process comprises: feeding the readily fermentable sugar material into the fermentation vat comprising a slurry of fermenting organism; feeding the protease into the fermentation vat comprising a slurry of readily fermentable sugars and fermenting organism before fermentation; and fermenting the readily fermentable sugar material into the fermentation product.

12. The process of claim 1, wherein ethanol is produced in a batch or fed batch fermentation process in a fermentation vat comprising sugar cane molasses, wherein the process comprises: feeding sugar cane molasses into the fermentation vat comprising a slurry of *Saccharomyces cerevisae* yeast; feeding the protease into the fermentation vat comprising a slurry of *Saccharomyces cerevisae* yeast and the sugar cane molasses before fermentation; and fermenting the sugar cane molasses into ethanol.

13. The process of claim 1 wherein the fermentation product is produced from readily fermentable sugar material by fermentation in a fermentation vat, wherein the process comprises: feeding the readily fermentable sugar material into the fermentation vat comprising a slurry of fermenting organism; and adding the protease into the fermentation vat during fermentation of the readily fermentable sugar-material into the desired fermentation product.

14. The process of claim 1, wherein ethanol is produced as a batch, fed batch, semi-continuous or continuous fermentation process in a fermentation vat comprising sugar cane molasses, wherein the process comprises: feeding the sugar cane molasses into the fermentation vat comprising a slurry of *Saccharomyces cerevisae* yeast; adding the protease into the fermentation vat during fermentation of the sugar cane molasses into ethanol.

15. The process of claim 1, comprising
i) feeding the readily fermentable sugar material into the fermentation vat comprising a slurry of fermenting organism;
ii) fermenting the readily fermentable sugar material into a desired fermentation product,
wherein feeding of the readily fermentable sugar-material is done by introducing a feeding stream into the fermentation vat; wherein
protease is mixed with the feeding stream before in step i); or
protease is added to fermentation vat after feeding.

16. The process of claim 1, wherein the protease is capable of hydrolyzing mannoprotein in fermented readily fermentable sugar material.

* * * * *

SEQUENCE LISTING

<160> NUMBER OF SEQ ID NOS: 7

<210> SEQ ID NO 1
<211> LENGTH: 177
<212> TYPE: PRT
<213> ORGANISM: Thermoascus aurantiacus

<400> SEQUENCE: 1

```
Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
        50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
        130                 135                 140

Ala Tyr Gly Tyr Gln Ala Ala Met Gly Leu Ser Ser Gln Ala Val
145                 150                 155                 160

Met Asn Ala Asp Thr Tyr Ala Leu Tyr Ala Asn Ala Ile Tyr Leu Gly
                165                 170                 175

Cys
```

<210> SEQ ID NO 2
<211> LENGTH: 412
<212> TYPE: PRT
<213> ORGANISM: Pyrococcus furiosus

<400> SEQUENCE: 2

```
Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140
```

-continued

Asp Ala Leu Ser Gln Ala Val Asn Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 3
<211> LENGTH: 438
<212> TYPE: PRT
<213> ORGANISM: Rhizomucor pusillus

<400> SEQUENCE: 3

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
            85                  90                  95

Gln Ala Ala His Glu Arg Asp Met Tyr Val Met Leu Asp Val Val Ala

```
            100                 105                 110
Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala
        435

<210> SEQ ID NO 4
<211> LENGTH: 583
<212> TYPE: PRT
<213> ORGANISM: Artificial Sequence
<220> FEATURE:
<223> OTHER INFORMATION: Hybrid Alpha-Amylase with catalytic core from
      Rhizomucor pusillus (AN782) and Linker+SBD from Aspergillus noger

<400> SEQUENCE: 4

Ala Thr Ser Asp Asp Trp Lys Gly Lys Ala Ile Tyr Gln Leu Leu Thr
1               5                   10                  15
```

-continued

Asp Arg Phe Gly Arg Ala Asp Asp Ser Thr Ser Asn Cys Ser Asn Leu
         20                  25                  30

Ser Asn Tyr Cys Gly Gly Thr Tyr Glu Gly Ile Thr Lys His Leu Asp
         35                  40                  45

Tyr Ile Ser Gly Met Gly Phe Asp Ala Ile Trp Ile Ser Pro Ile Pro
 50                  55                  60

Lys Asn Ser Asp Gly Gly Tyr His Gly Tyr Trp Ala Thr Asp Phe Tyr
 65                  70                  75                  80

Gln Leu Asn Ser Asn Phe Gly Asp Glu Ser Gln Leu Lys Ala Leu Ile
                 85                  90                  95

Gln Ala Ala His Glu Arg Asp Met Tyr Val Met Leu Asp Val Val Ala
             100                 105                 110

Asn His Ala Gly Pro Thr Ser Asn Gly Tyr Ser Gly Tyr Thr Phe Gly
         115                 120                 125

Asp Ala Ser Leu Tyr His Pro Lys Cys Thr Ile Asp Tyr Asn Asp Gln
 130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                 165                 170                 175

Trp Val Gly Asn Tyr Ser Phe Asp Gly Ile Arg Ile Asp Thr Val Lys
             180                 185                 190

His Ile Arg Lys Asp Phe Trp Thr Gly Tyr Ala Glu Ala Ala Gly Val
         195                 200                 205

Phe Ala Thr Gly Glu Val Phe Asn Gly Asp Pro Ala Tyr Val Gly Pro
 210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                 245                 250                 255

Glu Met Leu Gly Ser Asn Arg Asn Ala Phe Glu Asp Thr Ser Val Leu
             260                 265                 270

Thr Thr Phe Val Asp Asn His Asp Asn Pro Arg Phe Leu Asn Ser Gln
         275                 280                 285

Ser Asp Lys Ala Leu Phe Lys Asn Ala Leu Thr Tyr Val Leu Leu Gly
 290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
             325                 330                 335

Thr Ser Ser Asp Leu Tyr Gln Phe Ile Lys Thr Val Asn Ser Val Arg
         340                 345                 350

Met Lys Ser Asn Lys Ala Val Tyr Met Asp Ile Tyr Val Gly Asp Asn
     355                 360                 365

Ala Tyr Ala Phe Lys His Gly Asp Ala Leu Val Val Leu Asn Asn Tyr
 370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
             405                 410                 415

Val Ser Ser Asp Gly Thr Val Thr Phe Asn Leu Lys Asp Gly Leu Pro
         420                 425                 430

Ala Ile Phe Thr Ser Ala Thr Gly Gly Thr Thr Thr Thr Ala Thr Pro

```
                    435                 440                 445
Thr Gly Ser Gly Ser Val Thr Ser Thr Ser Lys Thr Thr Ala Thr Ala
        450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Thr Thr Thr Tyr Gly Glu
                        485                 490                 495

Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 5
<211> LENGTH: 515
<212> TYPE: PRT
<213> ORGANISM: Bacillus stearothermophilus

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
        210                 215                 220
```

```
Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
        260                 265                 270

Leu His Asn Tyr Ile Thr Lys Thr Asn Gly Thr Met Ser Leu Phe Asp
    275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 6
<211> LENGTH: 366
<212> TYPE: PRT
<213> ORGANISM: Meripilus giganteus

<400> SEQUENCE: 6

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Ser Thr Thr
    50                  55                  60

Phe Ser Leu Gln Thr Leu Asp Gly Gly Glu Asn Asp Gln Ser Pro Ser
65                  70                  75                  80
```

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
    290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365

<210> SEQ ID NO 7
<211> LENGTH: 371
<212> TYPE: PRT
<213> ORGANISM: Meripilus giganteus

<400> SEQUENCE: 7

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Ser Thr Thr
    50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu

-continued

```
                        85                      90                      95
Ala Thr Gly Val Pro Thr Thr Phe Ile Ser Val Gly Asp Asp Phe Gln
            100                     105                     110

Asp Gly Asn Leu Glu Gly Phe Leu Asp Ile Ile Asn Phe Leu Leu Gly
            115                     120                     125

Glu Ser Asn Pro Pro Gln Val Leu Thr Thr Ser Tyr Gly Gln Asn Glu
            130                     135                     140

Asn Thr Ile Ser Ala Lys Leu Ala Asn Gln Leu Cys Asn Ala Tyr Ala
145                     150                     155                 160

Gln Leu Gly Ala Arg Gly Thr Ser Ile Leu Phe Ala Ser Gly Asp Gly
                    165                     170                 175

Gly Val Ser Gly Ser Gln Ser Ala His Cys Ser Asn Phe Val Pro Thr
                180                     185                 190

Phe Pro Ser Gly Cys Pro Phe Met Thr Ser Val Gly Ala Thr Gln Gly
            195                     200                     205

Val Ser Pro Glu Thr Ala Ala Ala Phe Ser Ser Gly Gly Phe Ser Asn
        210                     215                     220

Val Phe Gly Ile Pro Ser Tyr Gln Ala Ser Ala Val Ser Gly Tyr Leu
225                     230                     235                 240

Ser Ala Leu Gly Ser Thr Asn Ser Gly Lys Phe Asn Arg Ser Gly Arg
                245                     250                     255

Gly Phe Pro Asp Val Ser Thr Gln Gly Val Asp Phe Gln Ile Val Ser
                260                     265                     270

Gly Gly Gln Thr Ile Gly Val Asp Gly Thr Ser Cys Ala Ser Pro Thr
            275                     280                     285

Phe Ala Ser Val Ile Ser Leu Val Asn Asp Arg Leu Ile Ala Ala Gly
        290                     295                     300

Lys Ser Pro Leu Gly Phe Leu Asn Pro Phe Leu Tyr Ser Ser Ala Gly
305                     310                     315                 320

Lys Ala Ala Leu Asn Asp Val Thr Ser Gly Ser Asn Pro Gly Cys Ser
                325                     330                     335

Thr Asn Gly Phe Pro Ala Lys Ala Gly Trp Asp Pro Val Thr Gly Leu
            340                     345                     350

Gly Thr Pro Asn Phe Ala Lys Leu Leu Thr Ala Val Gly Leu Arg His
        355                     360                     365

Gln His Gln
    370
```